US008764695B2

(12) United States Patent
Eliaz

(10) Patent No.: US 8,764,695 B2
(45) Date of Patent: Jul. 1, 2014

(54) REDUCTION OF GALECTIN-3 LEVELS BY PLASMAPHERESIS

(71) Applicant: Isaac Eliaz, Sebastopol, CA (US)

(72) Inventor: Isaac Eliaz, Sebastopol, CA (US)

( * ) Notice: Subject to any disclaimer, the term of this patent is extended or adjusted under 35 U.S.C. 154(b) by 6 days.

(21) Appl. No.: 13/629,932

(22) Filed: Sep. 28, 2012

(65) Prior Publication Data

US 2014/0094763 A1  Apr. 3, 2014

(51) Int. Cl.
| | | |
|---|---|---|
| *A61M 1/14* | (2006.01) | |
| *A61M 1/16* | (2006.01) | |
| *A61M 1/34* | (2006.01) | |
| *A61M 1/36* | (2006.01) | |
| A61M 1/38 | (2006.01) | |

(52) U.S. Cl.
CPC ............. *A61M 1/3472* (2013.01); *A61M 1/14* (2013.01); *A61M 1/16* (2013.01); *A61M 1/34* (2013.01); *A61M 1/3496* (2013.01); *A61M 1/3679* (2013.01); *A61M 1/36* (2013.01); *A61M 1/38* (2013.01)
USPC ....... 604/4.01; 604/5.01; 604/5.02; 604/5.04; 604/6.01; 604/6.04; 604/6.09

(58) Field of Classification Search
CPC ........... A61M 1/14; A61M 1/16; A61M 1/34; A61M 1/3496; A61M 1/3472; A61M 1/36; A61M 1/38; A61M 2001/14; A61M 2001/16; A61M 2001/34; A61M 2001/3472; A61M 2001/3486
USPC ........... 604/4.01, 5.01, 5.02, 5.04, 6.01, 6.04, 604/6.09
See application file for complete search history.

(56) References Cited

U.S. PATENT DOCUMENTS

| | | | |
|---|---|---|---|
| 3,625,212 A | 12/1971 | Rosenberg et al. | |
| 4,531,932 A | 7/1985 | Luppi et al. | |
| 6,245,038 B1 | 6/2001 | Borberg et al. | |
| 6,274,566 B1 | 8/2001 | Eliaz et al. | |
| 6,462,029 B1 | 10/2002 | Eliaz | |
| 6,627,151 B1 | 9/2003 | Borberg et al. | |
| 8,192,974 B1 | 6/2012 | Guo et al. | |
| 8,197,430 B1 * | 6/2012 | Lentz | 604/6.01 |
| 2002/0143283 A1 * | 10/2002 | Braverman et al. | 604/5.01 |
| 2003/0223969 A1 * | 12/2003 | Humes | 424/93.7 |
| 2004/0115278 A1 * | 6/2004 | Putz et al. | 424/489 |
| 2004/0147730 A1 * | 7/2004 | Nilsson et al. | 536/18.7 |
| 2004/0199099 A1 * | 10/2004 | Matson et al. | 604/6.09 |
| 2004/0223971 A1 * | 11/2004 | Chang et al. | 424/155.1 |
| 2005/0158321 A1 * | 7/2005 | Hurez et al. | 424/146.1 |
| 2005/0265996 A1 * | 12/2005 | Lentz | 424/141.1 |
| 2006/0129082 A1 * | 6/2006 | Rozga | 604/6.04 |
| 2006/0163138 A1 * | 7/2006 | Radunsky et al. | 210/321.6 |
| 2007/0049551 A1 | 3/2007 | Eliaz | |
| 2007/0258983 A1 * | 11/2007 | Brady et al. | 424/140.1 |
| 2011/0294755 A1 | 12/2011 | Eliaz | |
| 2012/0164628 A1 * | 6/2012 | Duffin et al. | 435/5 |

OTHER PUBLICATIONS

N. Rubinstein, J.M. Ilarregui, M.A. Toscano, G.A. Rabinovich. "The role of galectins in the initiation, amplification and resolution of the inflammatory response." Tissue Antigens, vol. 64, Issue 1, pp. 1-12, Jul. 2004. DOI: 10.1111/j.0001-2815.2004.00278.x.*
U.S. Appl. No. 61/568,210, filed Dec. 8, 2011, Eliaz.
Sarter, et al., "Autoantibodies Against Galectins are Associated with Antiphospholipid Syndrome . . . ", Glycobiology, Aug. 11, 2012.
Young, et al., "Functional Characterization of an Eosinophil-Specific Galectin, Ovine Galectin-14", Glycoconi J., May 2009;26(4):423-32.
Panoulas, et al., "Galectin-2 (LGALS2) 3279C/T Polymorphism May be Independently Associated with . . . " Clin. Exp. Hypertens, Apr. 2009;31(2):93-104.
Vander Laan, et al., "Galectin-2 Expression is Dependent on the rs7291467 Polymorphism . . . ", Eur. Heart J., May 2012;33(9):1076-84.
Gitt, et al., "Galectin-4 and Galectin-6 are Two Closely Related Lectins Expressed in Mouse Gastrointestinal Tract", J. Biol. Chem., Jan. 30, 1988;273(5):2954-60.
Stancic, et al., "Galectin-4, A Novel Neuronal Regulator of Myelination", Glia. May 2012;60(6):919-35.
Devouassous, et al., "Galecin-10 mRNA is Overexpressed in Peripheral Blood of Aspirin-Induced Asthma", Allergy, Jan. 2008;63(1):125-31.
Chua, et al., "Galectin-10, A Piotential Biomarker of Eosinophilic Airway Inflammation", PloS. One, 2012;7(8):e42549.
De Re V., et al., "Glaectin-10, Eosinophils, and Celiac Disease", Ann. N.Y. Acad. Sci., Sep. 2009;1173:357-64.
Hoorens, et al., "Galectin-11 Induction in the Gastrointestinal Tract of Cattle Following Nematode . . . ", Parasite Immunol. Dec. 2011;33(12)669-78.

(Continued)

*Primary Examiner* — Adam Marcetich
(74) *Attorney, Agent, or Firm* — Alchemy-Partners, PC; Steven B. Kelber

(57) ABSTRACT

The invention is directed to the removal of serum gal-3 from circulation by plasmapheresis using gal-3 binding agents in either a fixed bed, or in a form easily removed, such as by being complexed with magnetic particles. This method, on its own, brings a sharp reduction and relief from the inflammation and fibroses that can be induced by circulating gal-3. The process may be combined with the administration of gal-3 binding agents, such as modified citrus pectin, to further lower unbound gal-3 levels, to the point where gal-3 in the tissues may be addressed. This method may also be combined with removal of TNF receptors to provide an effective treatment for cancer.

23 Claims, No Drawings

(56) References Cited

OTHER PUBLICATIONS

Hotta, et al., "Galectin-12, An Adipose-Expressed Galectin-Like MOlecule Possessing . . . " J. Biol. Chem., Sep. 7, 2001;276(36):34089-97.

Balogh, et al., "Placental Protein 13 (PP13/galecin-13) Undergoes Lipid Raft-Associated Subcellular . . . ", Am. J. Obstet. Gynecol., Aug. 2011;205(2):156.e1-14.

Swaminathan, et al., "Selective Recognition of Mannose by the Human Eosinophil Charco-Leyden Crystal Protein . . . " Biochemistry, Nov. 16, 1999;38(46):15406.

Randall, et al., "Age-Related Susceptibility to Severe Malaria Associated with Galectin-2 in Highland Papuans", JID 2010:202 (Jul. 1).

Gupta, et al., "Allograft Rejection is Restrained by Short-Lived TIM-3+PD-1+Foxp3 + Tregs", J. Clin. Invest. doi:10.1172/JC145138, Jul. 2, 2012.

McGrath, et al., "The Role of Coinhibitory Signaling Pathways in Transplanation and Tolerance", Frontiersin. Mar. 2012, vol. 3, Article 47.

Okagawa, et al., "Increased Bovine Tim-3 and Its Ligand Expressions During Bovine Leukemia Virus Infection", Veterinary Research 2012, 43:45.

Toussaint, et al., "Galectin-1, A Gene Preferentially Expressed as the Tumor Margin Promotes Glioblastoma Cell Invasion", Molecular Cancer 2012, 11:32.

Vaitaitis, et al., "Galectin-9 ControlsCD40 Signaling Through a Tim-3 Independent Mechanism . . . " PLoS One, Jun. 2012, vol. 7, Issue 6.

Barrow, et al., "Serum Galectin-2, -4 and -8 are Greatly Increased in Colon and Breast Cancer . . . ", Clin Cancer Res., 2011 No. 15;17(22):7035-46.

Alves, et al., "Significance of Galectin-1, -3, -4 and -7 in the Progression of Squamous . . . ", Pathol. Res. Pract. Apr. 15, 2011;207(4):236-40.

Zhu, et al, "Roles of Galectin-7 and S100A9 in Cervical Squamous Carcinoma: . . . ", Int. J. Cancer, Aug. 3, 2012. doi: 10.1002.

Than, et al., "Functional Analyses of Placental Protein 13/galectin-13", Eur. J. Biochem., Mar. 2004;271(6): 1065-78.

Lewis, et al., "Galectin 15 (LGALS15): a Gene Uniquely Expressed in the Uteri of Sheep . . . " Biol. Reprod. Dec. 2007;77(6):1027-36.

Pal,et al, "Non-Synonymous Single Nucleotide Polymorphisms in Genes for Immunoregulatory . . . " Biochim. Biophys. Acta. Oct. 2012;1820(10): 1512-8.

Janko, et al., "Autoantibodies Against Galectin-2 Peptides as Biomarkers for the Antiphospholipid Syndrome", Lupus, Jun. 2012:21(7):781-3.

Gal, et al., "Open Wound Healing In Vivo: Monitoring Binding and Presence of Adhesion/Growth . . . " Acta Histochem. Cytochem. Oct. 26, 2011,44(5):191-9.

St-Pierre, et al., "A Distinctive Role for Galectin-7 in Cancer?", Front Biosci. Jan. 1, 2012;17:438-50.

Randall, et al.,"Age-Related Susceptibility to Severe Malaria Associated With Galectin-2 in Highland Papuans", J. Infect. Dis. Jul. 1, 2010;202(1):117-24.

\* cited by examiner

REDUCTION OF GALECTIN-3 LEVELS BY PLASMAPHERESIS

PRIORITY DATA AND INCORPORATION BY REFERENCE

This application claims benefit of priority to U.S. Provisional Patent Application No. 61/568,210 filed Dec. 8, 2011 which is incorporated by reference in its entirety.

BACKGROUND OF THE INVENTION

1. Field of the Invention

This invention pertains to treatment of disease and biological conditions mediated at least in part by one or more galectins. Galectins are a family of lectins (sugar binding proteins) that are characterized by having at least one carbohydrate recognition domain (CRD) with an affinity for beta-galactosides. These proteins were recognized as a family only recently, but are found throughout the animal kingdom, and are found in mammals, birds, amphibians, fish, sponges, nematodes and even fungi. This application focuses on galectins in mammals, and in particular, humans. Although the invention herein may be employed with both companion animals (e.g., pets such as dogs and cats) and commercial animals (such as cows, pigs and sheep) the methods and subject matter addressed herein are particularly focused on the treatment of humans.

Galectins mediate and modulate a wide variety of intracellular and extracellular functions, and thus are both expressed within the cell and frequently targeted to a specific cytosolic site, and secreted from the cell, for distribution extra-cellularly, as a component of human plasma. Among the many functions that are mediated by extracellular galectins are inflammation, fibrosis formation, cell adhesion, cell proliferation and metastatic formation (cancer) and immunosuppression.

Galectins are a family of fifteen (15) carbohydrate-binding proteins (lectins) highly conserved throughout animal species. Most galectins are widely distributed, though galectin-5, -10 and -12 show tissue-specific distribution. While galectins are variably expressed by all immune cells, they are upregulated in activated B and T cells, inflammatory macrophages, natural killer (NK) cells, and FoxP3 regulatory T cells. Galectins contain a variety of structural arrangements, but a relatively conserved carbohydrate recognition domain (CRD). The majority of galectins display a single CRD, and are biologically active as monomers (galectin-5, -7 and -10), or require homodimerization for functional activity (galectin-1, -2, -11, -13, -14 and -15). Alternatively, tandem-repeat-type galectins (galectin-4, -8, -9, and -12) contain two CRDs separated by a short linker peptide, while galectin-3 (chimeric type) has a single CRD fused to a non-lectin domain that can be complexed with other galectin-3 monomers to form an oligomeric pentamer. Of note, some galectins, such as galectin-10, bind to mannose-containing glycans. Among the family of galectins -1, -3, and -9 are particularly important as potential therapeutic targets, and -2, -4, -5, -6, -7, -8, -10, -11, -12, -13, -14, and -15 also appear implicated in a variety of biological pathways associated with morbidity and mortality.

Thus, galectin-7 has been implicated in the development of certain forms of cancer. St. Pierre et al, *Front. Biosci.*, 1:17, 438-50 (2012) and in a variety of specific cancers, including gal-2, -4 and -8 in the context of colon and breast cancer, Barrow et al, *Clin. Cancer Res.* 15; 17 (22) 7035-46 (2011). Squamous cell carcinoma of the tongue, Alves et al., *Pathol. Res. Pract.* 15; 207 (4) 236-40 (2011) has been shown to be associated with elevated levels of gal-1, -3 and -7, while cervical squamous carcinoma has been shown linked to gal-7 levels, Zhu et al, *Int. J. Cancer*, (August, 2012). A number of galectins, including gal-15, gal-13 and gal-10 have been demonstrated to be linked to implantation and pregnancy concerns. See, e.g., Than et al, *Eur. J. Biochem.* 271(6) 1065-78 (2004), Lewis et al, *Biol. Reprod.* 77(6); 1027-36 (2007). A number of galectins, including gal-2, 3, 8 and others have been identified as correlating with various autoimmune disorders, such as lupus. Salwati et al, *J. Infect. Dis.* 1; 202(1) 117-24 (2010), Pal et al, *Biochim. Biophys. Acta.*, 1820 (10) 1512-18 (2012) and Janko et al, *Lupus* 21(7):781-3 (2012). Elevated levels of a number of galectins, including gal-3, are associated with inflammation and fibroses encountered in wound healing and the like. Gal et al, *Acta. Histochem. Cytochem.* 26:44(5); 191-9 (2011).

Quite obviously, mediation of inflammatory and fibrotic pathways makes galectins critical elements of a wide variety of disease, injury and trauma related phenomena. In many cases, the presence of unwanted concentrations of galectins can aggravate a disease condition or trauma situation, or interfere with attempts to treat diseases, such as cancer or congestive heart failure. Among the family of galectins recognized as active intracellularly in humans, galectin-1, galectin-3 and galectin-9 are of particular interest. As indicated above, these proteins are generally referred to, and referred to herein as, gal-1, gal-3 and gal-9. A wide variety of conditions in humans, ranging from problems in conceiving to asthma to chronic heart failure to cancer to viral infection to stroke and beyond are mediated or aggravated by higher than normal concentrations of galectins. Thus, among other galectins, gal-3 is particularly prominent in fibrosis, inflammation and cell proliferation, while gal-1 also plays a role in the immunosuppression required for a successful pregnancy. Gal-1 is also thought to be involved in the differentiation of nerve cells. Gal-9 has been shown to be involved in the control of lesions arising from immunoinflammatory diseases, and is generally implicated in inflammation—gal-9 apparently plays a role in eosinophil recruitment in inflammatory sites. It also appears to mediate apoptosis in certain activated cells.

While the discussion herein is applicable to circulating active gal-1, gal-3 and gal-9, and galectins in general where elevated circulating galectin levels are associated with disease or injury conditions, more has been elucidated about the role of gal-3 in disease and trauma progression than any of the other galectins, and so it is exemplified herein. More specifically, this invention focuses on the removal of gal-3 from mammalian, particularly human, plasma. Gal-3 has been shown to be involved in a large number of biological processes, many of which are related to disease states of various kinds. Binding and blocking activity of gal-3 in the circulation, or removal of large amounts of gal-3 from circulation may therefore improve existing medical treatments, suppress and/or reduce inflammation and fibrosis resulting from others, and make it possible to intervene in various disease states not otherwise easily treated. The invention is equally applicable to the reduction in circulating levels of other galectins to address conditions mediated by those galectins.

This invention makes use of plasmapheresis, sometimes referred to as therapeutic plasma exchange, to control levels of gal-3, and more specifically biologically active galectin, in circulation. Plasma is lead through a fluid pathway and either intermixed with a gal-3 binding agent which can be separated from the plasma, or returned to the body with blocked inactivated gal-3, or lead past a solid support which binds gal-3, the plasma being subsequently returned to the body with a reduced level of gal-3.

2. Related Art

This application is related to U.S. patent application Ser. No. 13/153,648, filed Jun. 6, 2011. That application in turn claims priority benefit to U.S. patent application Ser. No. 11/485,955, filed Jul. 6, 2006. The content of both these patent applications is expressly incorporated herein-by-reference. In U.S. patent application Ser. No. 13/153,648 (U.S. Patent Publication US-2011-0294755 A1) a method of treating cell proliferation conditions, inflammation and aggravated fibroses is disclosed which involves the administration of an agent that can bind circulating gal-3, such as modified citrus pectin, or MCP, a citrus pectin which has a reduced molecular weight of twenty thousand (20,000) Daltons or less, preferably ten thousand (10,000) Daltons or so. MCP is available commercially from EcoNugenics of Santa Rosa, Calif. and is discussed in U.S. Pat. Nos. 6,274,566 and 6,462,029.

3. Background of the Technology

Gal-3 is approximately 30 kDa and, like all galectins, contains a carbohydrate-recognition-binding domain (CRD) of about one hundred thirty (130) amino acids that enable the specific binding of β-galactosides. Gal-3 is encoded by a single gene, LGALS3, located on chromosome 14, locus q21-q22. This protein has been shown to be involved in a large number of biological processes. The list set forth herein is exemplary only as new situations and roles for gal-3 are continually being revealed. Among the biological processes at the cellular level that have been shown to be mediated, at least in part, by gal-3, are cell adhesion, cell migration, cell invasion, cell activation and chemoattraction, cell growth and differentiation, cell cycle, and apoptosis.

Given gal-3's broad biological functionality, it has been demonstrated to be involved in a large number of disease states or medical implications. Studies have also shown that the expression of gal-3 is implicated in a variety of processes associated with heart failure, including myofibroblast proliferation, fibrogenesis, tissue repair, inflammation, and ventricular and tissue remodeling. Elevated levels of gal-3 in the blood have been found to be significantly associated with increased morbidity and mortality. They have also been found to be significantly associated with higher risk of death in both acute decompensated heart failure and chronic heart failure populations.

Various investigations have shown elevated levels of gal-3 to aggravate a wide variety of disease conditions associated with cell proliferation. High levels of gal-3 are linked to cancer growth and cancer progression to a metastatic stage in a stunning variety of cancers. A number of cancers have been specifically linked to or associated with elevated gal-3 levels, including liver cancer, kidney cancer, breast cancer, prostate cancer, colon cancer, thyroid cancer, cancer of the gallbladder, nasopharyngeal cancer, lymphocytic leukemia, lung cancer, melanoma, multiple myeloma, glioblastoma multiforme, uterine cancer, ovarian cancer, cervical cancer, brain cancer and others. Elevated gal-3 levels have also been shown to interfere with or suppress conventional antineoplastic regimens, such as chemotherapeutic treatments like cis-platinum, doxorubicin and related chemotherapeutics.

Inflammation is a commonly encountered body condition—a natural response of the body to a variety of diseases and trauma. As with the other conditions noted above, gal-3 levels above normal levels are implicated in a wide variety of situations where harmful inflammation is encountered. Again, the list of conditions and disease states is too extensive to exhaust every possibility, but inflammatory conditions associated with elevated gal-3 levels include aggravated inflammation associated with non-degradable pathogens, autoimmune reactions, allergies, ionizing radiation exposure, diabetes, heart disease and dysfunction, atherosclerosis, bronchial inflammation, intestinal ulcers, intestinal inflammation of the bowels, cirrhosis-associated hepatic inflammation, parasitic infection associated inflammation, inflammation associated with viral infection, inflammation associated with fungal infection, inflammation associated with arthritis, with multiple sclerosis and psoriasis. Again, while inflammation is a pathway frequently employed by the body in responding to any number of challenges, elevated levels of gal-3 have been found to aggravate the inflammation, causing damage and injury leading to morbidity or mortality in a wide variety of situations that are otherwise manageable, including inflammation due to heavy metal poisoning and similar toxins, stroke and related ischemic injuries, liver inflammation due to acetaminophen, a number of T-cell mediated responses generally involved in autoimmune diseases and the like. Gal-3 is also involved with kidney injury and kidney disease, hepatitis, pulmonary hypertension and fibrosis, diabetes, and gastrointestinal inflammatory conditions such as Ulcerative colitis, Chrone's, Celiac, and others.

As noted, elevated levels of circulating, active gal-3 are associated with, and apparently aggravate, a number of inflammatory conditions, including those contributing to heart, kidney, lung, and liver disease. Gal-3 is also associated with a fibrotic formation, particularly in response to organ damage. Higher levels of circulating gal-3 are found to induce pathogenic fibroses in cardiovascular disease, gastroenterological disease, cardiovascular trauma, renal tissue trauma, brain trauma, lung trauma, hepatic tissue trauma, tissue damage due to radiation therapy and diseases and conditions of connective tissue and skin such as systemic sclerosis.

Accordingly, the art is replete with observations that elevated levels of gal-3, as well as gal-1 and gal-9, can complicate or exacerbate a wide variety of disease and injury conditions. It would be of value to find a way to control inflammation and formation of fibroses, where the inflammation and fibroses are injurious, particularly in the environments described above, and notably in cardiac care and other organ tissue disease and trauma. By the same token, it would be of value to control the cellular responses mediated by gal-3 that accelerate cell proliferation and transformation, including the formation and growth of tumors, the transformation of cancer cells and metastatic spread of cancer. Another goal in the art is to avoid the problem posed by the interference in the treatment of cancer by conventional agents, like bleomycin, Adriamycin, doxorubicin, cyclophosphamide and cyclosporine. Some of the side effects caused by these agents are gal-3 mediated, and can be addressed and ameliorated by the invention. Elevated gal-3 levels also appear to interfere with pharmaceuticals used in other applications, such as the antiarrhythmic drug amiodarone, and statin drugs.

Plasmapheresis is a blood separation technology, where blood is diverted from the body through a needle or catheter to a separator which removes blood cells and returns them to the body, leaving a plasma. This type of technique has been used historically in the treatment of autoimmune diseases, where the antibodies at issue are removed by contacting the plasma with the ligands to which they bind. The plasma is then augmented as required, with anticoagulants, therapeutics and associated elements, and returned to the body.

An early form of apparatus for plasmapheresis is set forth in U.S. Pat. No. 3,625,212, which describes measures to ensure return of treated plasma, as well as the separated blood cells, to the proper donor. U.S. Pat. No. 4,531,932 addresses plasmapheresis by centrifugation, the method used to separate out the red blood cells, on a rapid and near-continuous basis. U.S. Pat. Nos. 6,245,038 and 6,627,151 each describe a variety of methods of separating out plasma contents and returning the treated plasma to the patient after first removing red blood cells, in general, to reduce blood viscosity by removal of high molecular weight protein. While the invention that is the subject of this application focuses on the reduction in galectins circulating levels, such as gal-3 levels, and not high molecular weight proteins or directly addressing viscosity, the disclosure of these four (4) patents is incorporated herein-by-reference for their disclosure of available plasmapheresis techniques and apparatus which may generally be employed in this invention.

Prior to the development of this invention, those of skill in the art had experimented with the reduction of gal-3 levels in various respects. Thus, the activity of gal-3 in aggravating or promoting cancer, as well as the ability of a cancer to metastasize, is widely commented on in the literature following 2006. These literature findings stress repeatedly the importance of binding or reducing the circulating concentration or titer of gal-3, and/or inactivating gal-3 through gal-3 binders such as PectaSol-C MCP. See, for example, Wang et al, *Cell Death and Disease*, 1-10 (2010) (gal-3 inhibition promotes treatment) and Yu et al, *J. Biol. Chemistry*, Vol. 282, 1, pp. 773-781 (2007) establishing that gal-3 interactions may enhance formation of cancer or transformation of metastatic cancer.

As disclosed and claimed in U.S. Pat. No. 6,274,566, Gal-3 binders such as Modified Citrus Pectin and other compounds can bind to circulating tumor cells (CTC's) and prevent them from creating new metastasis. These CTC's are often implicated in mutations and a more aggressive disease. Cancer stem cells that may also be circulating and get stimulated under conditions of stress and inflammation, provide gal-3 another mechanism for aggravating cancer. The method of these prior cases may be used in conjunction with the invention of this application. In particular, when there are a high number of gal-3 molecules circulating in the blood stream it makes it more difficult for the gal-3 binders to target these CTCs. In this respect, gal-3 molecules serve as decoy molecules. The decoy prevents, in this particular application of the invention, binding of the cancer cells in the circulatory or lymph system, as opposed to tissue level gal-3.

As a consequence, reports link acceleration of cancer formation and transformation to circulating gal-3 concentrations, and suggest that reducing gal-3 circulating concentrations, reducing its free expression or otherwise reducing available gal-3 or gal-3 interactions improves cancer prognosis. Zhao et al, *Cancer Res*, 69, 6799-6806 (2009), Zhao et al, *Molecular Cancer* 9, 154, 1-12 (2010) and Wang et al, *Am. J. of Pathology*, 174, 4, 1515-1523 (2009) wherein siRNA-induced reduction of gal-3 is shown to slow the course of prostate cancer. Similarly, high-risk bladder cancer recurrence and prognosis is related indirectly to gal-3 levels. Rodriguez et al, *J. Curr. Opin. Urol.* 22(5):415-20 (2012) and Raspollini et al, *Appl. Immunohistochem. Mol. Morphol.* (July 2012). Clearly, there is substantial literature that supports the conclusion that reducing circulating gal-3, either by blocking its expression, or by binding it, is important in controlling cancer, both in tissue and in circulation.

Circulating gal-3 is empirically implicated in a wide variety of biological conditions, however. Cardiac fibrosis is gaining significant attention as a complicating risk factor in cardiac disease, and in particular, chronic heart failure (CHF). Lok et al, *Clin. Res. Cardiol*, 99, 323-328 (2010). DeFillipi et al, *U.S. Cardiology*, 7,1, 3-6 (2010) clearly indicate that circulating gal-3 is an important factor in fibrosis of many organs and organ systems, and that reducing circulating gal-3 may have an important role in remediating cardiac injury and progression to heart failure (HF). Similarly, Psarras et al, *Eur. Heart J.*, Apr. 26, 2011 demonstrate that reduction in gal-3 levels in the myocardium may reduce fibrosis in the heart and improve outlook. De Boer et al, *Ann. Med.*, 43,1, 60-68 (2011) identify gal-3 as a key indicator in cardiac health. Shash et al, *Eur J. Heart Fail.*, 12, 8, 826-32 (2011) identify gal-3 levels as a key agent in heart failure through fibrosis. De Boer et al., *Eur. J. Heart Fail.*, 11, 9, 811-817 (2009) link an increase in gal-3 expression and presence to heightened fibrosis, and heart failure. The same article links gal-3 to inflammation. Inflammation is the hallmark of arteriosclerosis and therefore gal-3 levels also contribute to coronary artery disease, peripheral artery disease, strokes, and vascular dementia.

Fibrosis and inflammation, both mediated to some degree by gal-3 (cellular or circulating) are implicated in a variety of conditions of the mammalian body, not just cardiac injury and heart failure. The binding of gal-3 achieved by administration of low molecular weight pectins (at least, as reflected in U.S. patent application Ser. No. 11/485,955, 10,000-20,000 Daltons molecular weight such as PectaSol-C MCP) is effective in reducing trauma due to kidney injury. Kolatsi-Jannou et al, *PlusOne*, 6, 4, e18683 (2011). Reducing circulating gal-3 levels may be effective in reducing fibrosis in the lungs and associated asthma. Cederfur et al, *Biochim. Biophys. Acta*. 1820(9):1429-36 (2012). The reduction in circulating gal-3 levels is also indicated to reduce inflammation associated with type 2 diabetics, and similar metabolic diseases, as well as obesity. Weigert et al, *J. Endocrinol. Metab*. 95, 3,1404-1411(2010). Thus, high levels of gal-3 have been linked to thyroid cancer, Sethi et al, *J. Exp. Ther. Oncol.*, 8, 4,341-52 (2010) and reduction of gal-3 expression and circulation may delay or reduce tumor cell transformation. Chiu et al, *Am J. Pathol*. 176, 5, 2067-81 (2010).

As noted, gal-3 is implicated in a wide variety of biological conditions, and a reduction in gal-3 activity, such as that which can be achieved by gal-3 binding with PectaSol-C MCP and similar low molecular weight pectins may be of value in treating gastric ulcerative conditions. Srikanta, *Biochimie*, 92, 2, 194-203 (2010) Kim et al, *Gastroenterology*, 138, 1035-45 (2010) indicate that reducing gal-3 levels may be of therapeutic value in reducing gastric cancer progression. By the same methodology, reducing gal-3 levels sensitizes gastric cancer cells to conventional chemotherapeutic agents. Cheong et al, *Cancer Sci.*, 101, 1, 94-102 (2010). Gal-3 is implicated in a wide variety of gastrointestinal conditions. Reducing gal-3, by binding for example, may reduce inflammation in the gut mucosa, making MCP an important agent for treatment of ulcerative colitis, non-specific colitis and ileitis, Crohn's disease, Celiac disease, and gluten sensitivity. Fowler et al, *Cell Microbiol.*, 81,1,44-54 (2006).

Biliary artesia, a liver disease, is associated with extensive fibrosis of the liver linked with elevated gal-3 levels. Honsawek et al, *Eur. J. Pediatr. Surg.*, April, 2011. Reduction of gal-3 levels resulted in a general improvement in hepatic health, including reducing inflammation, hepatocyte injury and fibrosis. Federici et al, *J. Heptal.*, 54, 5, 975-83 (2011). See also, Liu et al, *World J. Gastroenterol*. 14,48, 7386-91 (2008) which reported, following Applicant's teaching in 2005 and 2006 to administer low molecular weight MCP, that MCP inhibited liver metastases of colon cancer and reduced gal-3 concentrations. MCP, or other gal-3 binders, may be used for prevention of liver inflammation, liver fibrosis and liver cirrhosis as well as post-disease liver damage, including the various viral hepatitis diseases (A, B, C, and others) and may be used as well in the treatment of parasitic and chemical hepatitis, chemical liver damage, and others. Gal-3 levels are implicated in a wide variety of liver associated ailments. Thus, gal-3 may be important in the control of Niemann-Pick disease type C, which is a lysosomal disorder characterized by liver disease and progressive neurodegeneration. Cluzeau et al, *Hum. Mol. Geent.* 14; 21 (16) 3632-46 (2012). There is increasing evidence that elevated gal-3 levels are tied to acetaminophen-induced hepatotoxicity and inflammation. Radosavljeci et al, *Toxicol. Sci.,* 127:609-19 (2012). Reduction in gal-3 levels may improve treatments. Dragomir et al, *Toxicol. Sci.* 127(2):609-19 (2012).

While administration of modified citrus pectin, or a similar binding agent, continues to be a promising therapy of inhibition of damage, and repair of damage, induced by gal-3, the inventor has continued to work to find other methods of providing faster or more profound relief. It has now been found that by selective use of certain gal-3 binding molecules, gal-3 and specifically biologically active gal-3 can be specifically removed from the plasma in significant amounts. Return of the plasma with a reduced titer of active gal-3 offers immediate opportunities for therapy and intervention that may be different from, or more profound than, the reduction achieved by administration of binding molecules to a mammal in need of same. By removing the circulating gal-3 molecules the invention removes these protective but potentially harmful molecules from the circulation. In addition, it allows targeted gal-3 blockers such as MCP, and possibly other oligo-saccharides and various pharmaceutical agents to be developed to better attach to the gal-3 on the cell surface and on the tissue level. As the expression of gal-3 is increased in the injured and inflamed tissue, such as remodeled cardiac muscle or cancer tissue, by removing the circulating gal-3, the gal-3 binding agent can more effectively bind to the Gal-3 in the target tissue.

SUMMARY OF THE INVENTION

The invention resides in the removal of biologically active gal-3 from a mammal's circulation by plasmapheresis. The mammal may be a human, a primate, a model such as a rat or mouse, a commercial animal such as a cow or pig or goat, or a companion animal such as a dog or cat. Non-human mammalian animals for treatment include primates, both as models and as test beds for treatments and intervention that may benefit from removal of gal-3 from circulation. Removal is achieved by plasmapheresis, a process traditionally developed and used to remove antibodies from the circulation of those suffering from autoimmune disorders and the like.

In plasmapheresis, blood is removed from the patient, and blood cells are separated out from the plasma. The blood cells are returned to the body's circulation, diluted with fresh plasma or a substitute. Conventional plasmapheresis methods and medications that can include blood thinners are utilized. While in typical plasmapheresis, the plasma is run over proteins to which the target antibodies bind, in this particular case, the plasma is returned to the blood with the antibodies, cytokines, lymphocytes and other blood components, after having had gal-3 selectively removed or inactivated by contact with gal-3 binding molecules. In the case of autoimmune diseases, the removal of Glaectin-3 from the plasma can be an adjuvant therapy added to the traditional plasmaphoresis performed for such patients.

This treatment may be used for all the conditions where gal-3 levels are elevated in the blood or serum or where expression of gal-3 in the tissues is too high. Tissues will shed excess gal-3 into the blood stream where it can be removed through this invention. Treatment can be varied depending on the patient, the severity of the condition and the rate of the mammalian patient's expression of gal-3. Ordinarily, treatment every two to four weeks is contemplated until the condition is resolved, but treatment may be daily where required, or at any frequency there between. Daily treatment includes one or more plasma exchange sessions in a given day, or continuous plasmapheresis over a multiple hour period in acute conditions. Treatment can be administered on an acute or a chronic basis. Advantageously, this treatment is combined with the administration of gal-3 blockers and inhibitors, such as disclosed in U.S. patent application Ser. No. 13/153,618. Although modified citrus pectin is a target inhibitor, other gal-3 inhibitors, such as other modified carbohydrates, including lactulosyl-1-leucine, Dermotte et al, Can. Res., 70 (19):476-88 (October 2010) as well as antibodies specific for gal-3, and other antagonists like very low molecular weight pectin weighing as low as 1 KD, GCS-100, Streetly et al, Blood, 115(19):3939-48 (published Feb. 26, 2010 as an abstract) may be used. GCS is a polysaccharide derived from MCP, as opposed to reduced MCP. A large variety of gal-3 binding antibodies are commercially available, from suppliers including abcam (ab2473), Novus Biologics (NB 100-91778) and Abgent (AJ13129). Other galectins-3 specific antibodies may be used. By removing large levels of plasma active gal-3 from the blood, the disease and injury due to inflammation or fibroses may be reduced, and the progression of cancer may be impeded. Similarly, conventional therapeutic treatments may be rendered more effective.

In a preferred embodiment, at the same time active gal-3 is removed, soluble TNF receptors, both R-1 and/or R-2 at different ratios based on the condition, are removed, through the same process, by running the plasma fluid over a bed of binding agents of TNF receptors. TNF can then directly target cancer cells or other targets as an effective treatment. The reduction of active gal-3 in both the circulation and the tissue level will allow TNF to exert its beneficial effects with a reduced amount of inflammation and fibrosis which limits its use. Wu et al, *Arch. Dermatol.* 20:1-7 (2012). The effective removal of serum gal-3 also enhances chemotherapy, particularly, but not exclusively, when combined with TNF receptor removal. Chemotherapy enhancement will take place by effective removal of serum gal-3, reducing drug resistance, even if no TNF receptors were removed from the circulation. Yamamato-Sugitani et al, *PNAS,* 18:108(42), 178468-73 (2012). Gal-3 interferes with platinum-based chemotherapy and other anti-cancer agents, and increases cell adhesion, and angiogenesis. Wu et al, *Cell Oncol.* 35(3):175-80 (2012). In addition, removal of gal-3, by plasmapheresis alone, or together with administration of circulating gal-3 binders like low molecular weight modified citrus pectin, may effectively treat the diseases and conditions addressed above. In addition, this can be further enhanced by combining it with other therapies, one example being chemotherapy in cancer.

Typical circulating gal-3 level averages for a Caucasian adult range from 7 on up to about 20 ng/ml, with a value of 12-15 nanograms of gal-3 per milliliter of serum being a representative and reported value. Patients at risk, including those with advanced illnesses, exhibit levels, without treatment, that can be much higher than that patient's average or normal level. In accordance with the invention, individuals facing serious illness or continued disability due to gal-3 mediated fibrosis, gal-3 mediated inflammation, and cancer growth, transformation and metastases associated with elevated gal-3 levels are treated by plasmapheresis to achieve a significant reduction in circulating gal-3 titer.

By significant reduction in circulating gal-3 levels, inflammation and/or fibrosis due to trauma or disease condition can be controlled. Similar reductions in gal-3 levels can aid in the control of the growth, spread and the transformation of various kinds of cancer. In general, a reduction of circulating gal-3 of at least ten percent (10%) is necessary to achieve significant progress in gal-3 mediated fibroses, and even more may be required in acute conditions involving inflammation, fibroses due to trauma or aggressive cancer. In functional terms, the reduction of gal-3 should be sufficient to reduce or inhibit the impact of gal-3 levels on inflammation and fibroses, or cancer growth and transformation, in said patient. Reduction in circulating gal-3 of at least twenty percent (20%), and in some cases at least forty percent (40%) or even fifty percent (50%), may be required on a sustained basis. Severe situations may require reduction in circulating gal-3 levels in a mammalian patient of greater than fifty percent (50%) of that patient's circulating gal-3 titer, on up to seventy-five percent (75%) or even more. While some level of gal-3 in circulation is required for homeostasis, in acute situations, reductions at least by eighty percent (80%) of circulating gal-3, on up to near total removal of gal-3 from serum, may be called for, as that level is quickly replenished by the body. Acute situations can be found in all sorts of individuals, but a representative example is hepatic inflammation or transformation in an aggressive cancer like pancreatic cancer or small cell lung carcinoma.

The gal-3 levels in races other than Caucasians and subjects may vary, but the target is to reduce gal-3 levels below the appropriate normal value. Target levels can vary based on the condition, age, gender, and other therapies involved. As a general matter, treatment of the patient according to this invention may begin with plasmapheresis designed to reduce the patient's gal-3 to a preselected value consistent with good health and homeostasis in that individual. In some cases, it may be necessary to repeat or extend that treatment to achieve even greater reductions.

This invention is straightforward in its application. It is recognizing how many different indications are served by this technology that is complex and startling. In the current invention, blood is removed from the patient according to well established protocols generally used for plasmapheresis. See, generally, Samuels et al, editors, *Office Practice of Neurology*, 1996. The removed blood is treated to remove blood cells from the plasma. These blood cells, together with an additional volume of plasma or plasma substitute, are returned directly to the patient. In a single session, two to four liters of plasma may be removed, filtered, and replaced. The blood can also be recycled and recirculated extra corporally, and filtered as needed, for a number of times (continuously) until the desired reduction in serum levels of galecitn-3 is achieved. Different serum levels can be targeted for different conditions. The blood cell-depleted plasma is then introduced to a chamber where gal-3 is removed or inactivated by binding antagonist, possibly creating a permanent bond that inactivates the gal-3. One of two alternative measures may be used to remove gal-3, although they may be combined. In a first alternative, the plasma is admixed with a particle which binds gal-3. Preferably, this is an antibody or similar ligand, or a polysaccharide derivative that is most preferably modified citrus pectin (MCP), but any agent that can bind gal-3 can be used. Methods of preparing low molecular weight pectins are known in the art, and set forth in U.S. patent application Ser. No. 13/153,648.

The binding agent is modified to be complexed with an agent that is easily removed. In one embodiment, this is a magnetic particle. After providing for adequate circulation time, a magnetic field is applied to the fluid comprising the plasma and the MCP complex, and the bound gal-3 can be drawn off. Different filters that incorporate gal-3 binders can be used in the plasmapheresis process.

In certain conditions such as cancer, the circulating gal-3 can be viewed as a sort of decoy released by the cancer cells. It has a protective quality as it doesn't allow the host, and doesn't allow gal-3 binders such as MCP, to reach the target tissue where galecin-3 is over expressed. It also induces inflammation and fibrosis and makes it more difficult for the host to bind to the gal-3 in the tissue and cell surface level. Removing the circulating gal-3 provides both a therapeutic treatment on its own and allows other agents to bind and inactivate the gal-3 in the target tissue level. This is similar to TNF Alpha and circulating TNF alpha receptors. Such plasmapheresis can be combined with plasmapheresis of other compounds, and can enhance an immune response and an anti-inflammatory response. The reduction of circulating gal-3 will allow one of skill in the art, typically a medical practitioner with at least five (5) years of experience in the field in addition to appropriate educational experience, to more easily neutralize and inactivate the tissue expressed gal-3, thus allowing for a local immune response with less inflammation and fibrosis. As such, it can be combined with removal of TNF Alpha receptors, both R-1 and R-2. It can also be combined with administration of TNF alpha or agents that enhance TNF alpha activity.

Removing or reducing the level of circulating galectin-3 can reduce the systemic and unwanted inflammatory process, resulting, as demonstrated in the kidney MCP study, with reduction in levels of IL-6, and consequently TNF alpha and TNF Kapa Beta.

Accordingly, the invention disclosed herein operates on two (2) levels:
 1. Direct reduction of circulating gal-3; and
 2. Ability to better target the gal-3 in the tissue level.

This has several consequences in terms of treatment effectiveness:
 A. By reducing the circulating gal-3, there can be greater shedding of the tissue gal-3 through greater gradient difference, resulting in reduced inflammation, fibrosis and remodeling in the tissue level.
 B. Reduction of secondary pro-inflammatory cytokines such as IL-6, TNF alpha, TNF Kapa beta, and others.
 C. It can allow a greater efficacy of circulating various gal-3 blockers in general, and specifically MCP and polyuronides under 40K Dalton.
 D. It can increase the efficacy of other therapies that are inhibited by excessive circulating gal-3.

In an alternative embodiment, the gal-3 comprising plasma may be run past a solid phase of immobilized gal-3 binding agents. MCP is one example and gal-3 specific antibodies, bound to a column or tube, are another. In the preferred embodiments, these two approaches to removal of gal-3 from circulation are combined. They can be combined in either order, but running the plasma past an immobile phase, followed by combining the plasma with an easily removable binding agent is preferred. Alternately the binding of an antagonist to gal-3 may be adequate to inactivate the molecule, and thus can be returned to the body without the step to remove it from the plasma.

The binding of gal-3 by a plasmapheresis element that will remove it from circulation is an event that will aid medical conditions over a wide variety of indications. On a broad scale, the indications are principally associated with inhibiting tumor growth and transformation (cancer), inflammation and fibrosis. These are implicated in specific indications such as, heart disease, kidney damage, liver damage, hepatic and renal disease, bladder disease, thyroid disease, pulmonary disease, gastrointestinal disease, immune response, stroke, persistent acute inflammation due to non-degradable pathogens, persistent foreign bodies, autoimmune reactions, hypersensitivities and allergies, pesticides, environmental toxins, and heavy metals, as well as heterogenic conditions such as radiation (examples being medical procedures such as various radiation therapies, exposure to ionizing radiation, nuclear radiation, cosmic radiation, electromagnetic radiation), chemotherapy damage, and post radiation and chemotherapy induced inflammation and fibrosis, post-surgery rise in inflammation, acute traumas such as accidents, and others.

Elevated circulating Gal-3 can change a localized situation, such as localized inflammation or fibrosis, and convert it into a larger, systemic problem. Thus, when gal-3 binds to components in the blood, which also bind toxic agents and the like, or similarly, when localized toxins are bound by gal-3, the damage potentially caused by these agents proximate to a localized injury or diseased tissue can become systemic. The same phenomenon is observed in connection with potentially metastatic cancer. Gal-3 is a generally adhesive molecule. Elevated gal-3 levels will accelerate the spread of cancer from a localized tumor to a system wide, multi-organ problem. Reducing elevated gal-3 levels below 15 or 12 ng/ml, by ten percent (10%) or more, will help to localize injury and damage, and maximize the benefit of unrelated therapeutic agents at the local injury or disease site.

As noted above, elevated gal-3 levels are associated with growth, transformation and metastatic migration of cancer cells across a wide variety of cancers, including liver cancer, kidney cancer, breast cancer, prostate cancer, colon cancer, thyroid cancer, cancer of the gallbladder, nasopharyngeal cancer, lymphocytic leukemia, lung cancer, melanoma, multiple myeloma, glioblastoma multiforme, uterine cancer, ovarian cancer, cervical cancer, and brain cancer among others, as well as reducing sensitivity in these cancers to conventional antineoplastic agents.

Elevated gal-3 levels are also associated with the development and extension of fibroses beyond normal and healthy levels, in situations associated with cardiovascular disease and heart failure, in tissue injury including brain, lungs, renal, hepatic, heart and gastroenterological situations as well as tissue damage due to radiation and chemotherapy exposure.

Above-normal gal-3 levels are also encountered in connection with inflammation. This can be disease or trauma associated inflammation, as well as persistent acute inflammation due to non-degradable pathogens, persistent foreign bodies, or autoimmune reactions, hypersensitivities and allergies, ionizing radiation, nuclear radiation and inflammation that may be associated with disease or organ failure modes, including diabetes (I and II), heart disease and dysfunction, atherosclerosis, asthma (bronchial inflammation), gastric and duodenal ulcers, intestinal inflammation in the bowels (inflammatory bowel diseases), hepatic inflammation associated with both alcohol and non-alcohol related cirrhosis and inflammation, liver infections such as viral hepatitis, among others. Other indications associated with inflammation and susceptible to treatment by plasmapheretic treatment to reduce gal-3 levels include a variety of parasite-induced conditions, such as trypanosomiasis, cerebral malaria, and inflammation and resistance to various infections including *Paracoccidiosis brasilensis* (fungal infection), schistosomiasis, granulatomatous bronchopneumonia, Lymes disease, Tuberculosis, etc. Reports of elevated gal-3 levels in connection with infection include *Candida albicans*, Reales-Calderon et al, *J. Proteomics*, 3:75(15) 4734-46 (2012), *Schistoma mansoni* (a parasitic infection) Brand et al, *Histol. Histopathol.*, 27(8) 1109-20 (2012) and many others, including bacterial infections like *Neisseria meningitides*, Quattroni et al, *Cell Microbiol.*, (July 2012). Prion infection, in CNS disease, has also been linked to gal-3 elevated levels. Mok et al, *Biochem. Bophys. Res. Commun.* 3:359:672-8 (2007). Elevated gal-3 levels are an important contributing factor in inflammation associated with arthritis, multiple sclerosis, Parkinson's, other neurological ailments; and other diseases of the skeletomuscular and skin systems, including inflammation and fibrosis related conditions such as psoriasis and aging of the skin. See, for instance, Ezzat et al, *Int. J. Rheum. Dis.*, 14(4):345-52 (2011) (arthritis), Gal et al, *Acta. Histochem. Cytochem.*, 44(5):191-9 (2011) and Liu et al, *Invest. Dermatol.*, 10.1038 (2012) (wound healing) and Larsen et al, *Dermatol. Sci.*, 64(2):85-91 (2011) (skin diseases). As noted above, these conditions may be treated by removal of biologically active, unbound gal-3 from circulation by this invention alone, or by removal from circulation combined with administration of gal-3 binding agents such as MCP to further address gal-3 mediated conditions.

Inflammation mediated at least in part by circulating gal-3 levels also plays a role in organic psychiatric and brain disorders. This kind of inflammation has been associated with a wide variety of conditions, such as schizophrenia. Muller et al., *Adv. Protein Chem Struct. Biol.*, 88, 49-68 (2012) and Palladino et al, *J. Neuroinflammation*, 22; 9, 206 (2012). Thus, reducing elevated gal-3 levels may be one method to assist in the control of psychiatric disorders of this type which are difficult to control by therapeutic intervention alone. Similarly, a condition receiving increasing attention, attention deficit hyperactivity disorder (ADHD) has been shown to be mediated to some degree by gal-3 expression. Wu et al, *Brain Pathol.*, 20(6), 1042-54 (2010). Elevated gal-3 expression levels, and the inflammation associated therewith, have also been linked to organic tissue damage, as well as psychiatric behavioral disorders. Thus, Alzheimer's Disease and enhanced Aβ amyloid deposits have been shown to be associated with pro-inflammatory conditions, such as those mediated by elevated gal-3 levels. Reale, et al, *Curr. Alzheimer Res.* 9(4), 447-57 (2012). Gal-3 has also been shown to be involved in the proper differentiation of oligodendrocytes controlling myelin sheath conditions, Pasquin et al, *Cell Death Differ.*, 18(11), 1746-56 (2012) and recovery and regrowth following traumatic brain injury. Venkatesan et al, *J. Neuroinflammation* 27(7) 32 (2010). Thus, in addition to being of importance in the control of inflammation in disease or injury conditions generally, reduction of circulating gal-3 levels through plasmapheresis may be of critical value in controlling for physical phenomena associated with disorders of the brain and central nervous system.

It should be noted that commonly, inflammation and fibrosis can be induced by deliberate treatment, not just trauma or disease condition. The removal of circulating, unbound gal-3 through this invention can be effective in reducing or preventing organ damage induced by chemotherapy and other pharmaceuticals. Some examples include bleomycin, which induces lung fibroses, and a wide variety of cardiac drugs such as amiodarone. Adriamycin and doxorubicin are widely prescribed and present cardiac inflammation and fibroses issues. *Bacillus* Calmette-Guerin washes to treat bladder cancer induce systemic inflammation and cyclophosphamide also induces bladder damage. Cyclosporine, a widely used immunosuppressant drug, and the active agent in Restasis™, induces kidney toxicity and inflammation. Studies indicate that the vast array of organ damage caused by prescribed pharmaceuticals is mediated, at least in part, by elevated gal-3 levels, and can be limited if not eliminated by the method of this invention.

In a preferred embodiment, the serum, after having circulating gal-3 reduced or removed, as described, is further treated before returning it to the patient's blood stream. Specifically, agents that may be more effective in the absence of, or in the presence of reduced levels of, galectin-3 are specifically added. This includes a wide variety of active agents, but specifically includes agents such as chemotherapeutic drugs and therapeutic agents for the various conditions. For example, an anti-inflammatory will work better, cardiac medications, any drugs delivered to address an issue where gal-3 is a contributing factor, or prevents effective delivery to the target tissue, will be enhanced by this process. These agents will then have the opportunity to work under an environment of lower levels of gal-3. Even if just for a few hours, they can exhibit full biological activity. Once inflammation, for example, is reduced, naturally less gal-3 is being produced and expressed by the target tissue resulting in lower circulating gal-3 on a long term basis.

Thus, while in one alternative, the invention involves long term or chronic plasmapheresis to maintain reduced gal-3 levels, the invention also contemplates intervention on a short term basis, both removing circulating gal-3 and providing agents otherwise inhibited by gal-3, to swiftly address inflammation in particular. Gal-3 levels can spike as a transient event, in response to trauma for example. Having a technique to rapidly lower gal-3 levels in the patient, coupled with administration of active agents that are ordinarily inhibited to some degree by high levels of gal-3, can offer a lifesaving technique.

Although Applicant does not wish to be confined to these few examples, a large number of conditions have been shown to be mediated by unbound gal-3, such that its removal, by the invention addressed herein, will aid in treatment. It has been demonstrated that reducing free gal-3 in humans can prevent renal fibrosis and inflammation following kidney injury. Both thyroid cancer and lung cancer treatment has been demonstrated to effectively improve by reducing gal-3 concentrations. Enhanced sensitivity to both radiation and chemotherapeutic intervention may be achieved by reducing circulating levels of active gal-3 through this invention.

Asthma, and related conditions primarily marked by exaggerated inflammation may be avoided or suppressed by removing circulating gal-3 through the process of this invention. These include inflammation of the gastrointestinal tract, and inflammation and the development of fibroses of the liver, interstitial cystitis, inflammation associated with brain and cognitive function, and others. Inflammation associated with parasite invasion may also be controlled by removal of gal-3, or reducing its circulating level through this invention. Other inflammation-associated diseases, such as diabetes and arthritis are similarly treated. These conditions may ideally be targets of this invention as well as administration of circulating gal-3 binding agents like MCP, and unrelated therapeutic agents.

While the present invention has been disclosed both generically, and with reference to specific alternatives, those alternatives are not intended to be limiting unless reflected in the claims set forth below. The invention is limited only by the provisions of the claims, and their equivalents, as would be recognized by one of skill in the art to which this application is directed.

What is claimed is:

1. A method of treating a condition in a mammal mediated at least in part by active galectin-3 in the blood, comprising: selecting a mammal in need of reduction of circulating levels of galectin-3; and conducting plasmapheresis on the blood of said mammal to reduce circulating levels of active gal-3, wherein said plasmapheresis is conducted so as to selectively remove galectin-3 (gal-3), such that at least ten percent of the circulating gal-3 in the serum of that individual is removed by said plasmapheresis.

2. The method of claim 1, wherein said method further comprises periodically monitoring the level of circulating gal-3 in said mammal, and repeating said plasmapheresis on said mammal when said level of gal-3 is above a preselected level of gal-3 for said individual consistent with that individual's gal-3 mediated disease state.

3. The method of claim 1, wherein the circulating level of galectin-3 in said mammal is reduced by at least twenty-five percent (25%).

4. The method of claim 3, wherein, upon return of said separated plasma to said mammal, the level of circulating gal-3 in said mammal is below 15 ng/ml.

5. The method of claim 1, wherein the circulating level of gal-3 is reduced by said plasmapheresis by about fifty percent (50%) of the level of gal-3 prior to said plasmapheresis.

6. The method of claim 1, wherein said individual's circulating gal-3 level is reduced by said method by at least seventy-five percent (75%).

7. The method of claim 1, wherein said step of conducting plasmapheresis comprises diverting a portion of said mammal's blood from said mammal's body to provide a volume of separated blood, removing red blood cells from said separated blood to provide separated plasma and returning said red blood cells to said mammal's circulation, contacting said separated plasma with moieties that bind gal-3, and separating out any such moieties and gal-3 bound by them from the rest of said separated plasma to provide a plasma with reduced levels of galectin-3, and returning said separated plasma with reduced levels of galectin-3 to said mammal's circulation.

8. The method of claim 7 wherein said moieties comprise antibodies which bind gal-3, carbohydrates which bind gal-3 and combinations thereof.

9. The method of claim 7, wherein said moieties are conjugated to an element that makes separation of said moiety and any gal-3 bound thereby from said separated plasma easier.

10. The method of claim 9, wherein said element is a column to which said moieties are affixed, a scaffold on which an array of said moieties is affixed, magnetically attractable particles, and mixtures thereof.

11. The method of claim 1, wherein said mammal is selected because it is in need of inhibition of the growth or spread of cancer mediated at least in part by gal-3.

12. The method of claim 11 wherein said cancer is liver cancer, kidney cancer, breast cancer, prostate cancer, colon cancer, thyroid cancer, cancer of the gallbladder, nasopharyngeal cancer, lymphocytic leukemia, lung cancer, melanoma, multiple myeloma, glioblastoma multiforme, uterine cancer, ovarian cancer, cervical cancer, or brain cancer.

13. The method of claim 11, wherein said mammal is receiving antineoplastic chemotherapy for cancer which therapy is inhibited by gal-3.

14. The method of claim 1, wherein said patient is selected because it is in need of inhibition of inflammation mediated by gal-3.

15. The method of claim 1, wherein said mammal is selected because it is in need of inhibition of development or extension of fibroses mediated by gal-3.

16. The method of claim 15, wherein said fibroses are associated with cardiovascular disease, gastroenterological disease, cardiovascular trauma, brain trauma, lung trauma, renal tissue trauma, hepatic tissue trauma, tissue damage due to radiation therapy and tissue damage due to chemotherapy.

17. The method of claim 14, wherein said inflammation is associated with non-degradable pathogens, autoimmune reactions, allergies, ionizing radiation, nuclear irradiation, diabetes, heart disease and dysfunction, atherosclerosis, bronchial inflammation, intestinal ulcers, intestinal inflammation of the bowels, hepatic inflammation, cirrhosis-associated hepatic inflammation, inflammation associated with parasitic infection, inflammation associated with viral infection, inflammation associated with fungal infection, inflammation associated with bacterial infection, arthritis associated inflammation, inflammation associated with organic psychiatric or brain disorders, multiple sclerosis, and psoriasis.

18. The method of claim 14, wherein said mediated by gal-3 is caused by administration of a pharmaceutical therapy received by said patient prior to practicing said method.

19. The method of claim 18, wherein said pharmaceutical therapy comprises bleomycin, amidoarone, Adriamycin, doxorubicin, cyclophosphamide and cyclosporine.

20. The method of claim 1, wherein said mammal is selected as in need of reduction of gal-3 levels after administering a pharmaceutical to said mammal, so as to improve the effectiveness of said pharmaceutical administered to said individual.

21. The method of claim 20, wherein said pharmaceutical is a statin, an antineoplastic chemical agent, an anti-inflammatory agent, a TNF blocker, or a TNFα activity promoter.

22. The method of claim 1, wherein before said serum returned to said patient it is admixed with a pharmaceutical agent whose activity is improved where galectins-3 levels are reduced.

23. The method of claim 22, wherein said pharmaceutical agent is an antineoplastic agent or an anti-inflammatory agent.

* * * * *